United States Patent
Cecil

(10) Patent No.: US 9,785,860 B2
(45) Date of Patent: Oct. 10, 2017

(54) REAL-TIME IMAGE ENHANCEMENT FOR X-RAY IMAGERS

(71) Applicant: THE CLEVELAND CLINIC FOUNDATION, Cleveland, OH (US)

(72) Inventor: Robert Cecil, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 21 days.

(21) Appl. No.: 14/800,956

(22) Filed: Jul. 16, 2015

(65) Prior Publication Data

US 2016/0019678 A1 Jan. 21, 2016

Related U.S. Application Data

(60) Provisional application No. 62/025,058, filed on Jul. 16, 2014.

(51) Int. Cl.

| | | |
|---|---|---|
| *G06T 5/00* | (2006.01) | |
| *A61B 6/00* | (2006.01) | |
| *G06K 9/52* | (2006.01) | |
| *G06T 7/00* | (2017.01) | |
| *G06T 5/20* | (2006.01) | |
| *A61B 6/03* | (2006.01) | |
| *A61B 6/02* | (2006.01) | |

(52) U.S. Cl.
CPC .............. *G06K 9/52* (2013.01); *A61B 6/5211* (2013.01); *A61B 6/5258* (2013.01); *G06T 5/003* (2013.01); *G06T 5/20* (2013.01); *A61B 6/025* (2013.01); *A61B 6/032* (2013.01); *A61B 6/502* (2013.01); *G06T 2207/10116* (2013.01); *G06T 2207/20192* (2013.01)

(58) Field of Classification Search
CPC ..... A61B 6/5258; A61B 6/5211; A61B 6/502; A61B 6/025; A61B 6/032; G06K 9/52; G06T 5/003; G06T 5/20; G06T 2207/10116; G06T 2207/20192
USPC ............................................. 382/132; 378/63
See application file for complete search history.

(56) References Cited

U.S. PATENT DOCUMENTS

| | | | |
|---|---|---|---|
| 5,271,064 A | 12/1993 | Dhawan et al. | |
| 2008/0266413 A1* | 10/2008 | Cohen | ....................... G06T 5/20 348/222.1 |

(Continued)

OTHER PUBLICATIONS

Krejci et al. "Enhancement of Spatial Resolution of Roentgenographic Methods Using Deconvolution." IEEE Nuclear Science Symposium Conference Record, Oct. 19, 2008, pp. 4124-4129.*

(Continued)

*Primary Examiner* — Jon Chang
(74) *Attorney, Agent, or Firm* — Tarolli, Sundheim, Covell & Tummino LLP

(57) ABSTRACT

Systems and methods are provided for an X-ray imaging system. An X-ray source is configured to provide X-ray radiation and has an associated focal spot. A detector is configured to generate a digital image representing attenuation of the X-ray radiation as it passes through a subject. An image enhancement component is configured to apply a separable deconvolution kernel, derived from an estimate of a point spread function associated with the focal spot as a vector function applied to the rows and subsequently to the columns of the digital image.

16 Claims, 2 Drawing Sheets

(56) References Cited

U.S. PATENT DOCUMENTS

| | | | |
|---|---|---|---|
| 2011/0032392 A1* | 2/2011 | Litvinov | G06T 3/4015 |
| | | | 348/241 |
| 2012/0257810 A1 | 10/2012 | Von Berg et al. | |
| 2016/0171667 A1* | 6/2016 | Tezaur | G06T 5/003 |
| | | | 382/275 |

OTHER PUBLICATIONS

Fisher et al. "Gaussian Smoothing", 2003—web document found at http://homepages.inf.ed.ac.uk/rbf/HIPR2/gsmooth.htm.*

Pei, Soo-Chang, and Ji-Hwei Horng. "Design of FIR bilevel Laplacian-of-Gaussian filter." Signal Processing 82.4 (2002): 677-691.

Sondes, Tebini, et al. "Directional Separable Kernel Family with Compact Support—SKCS—for de-noising image and preserving edges." Proceedings Engineering & Technology—vol. 2 (2013): 186-190.

* cited by examiner

REAL-TIME IMAGE ENHANCEMENT FOR X-RAY IMAGERS

RELATED APPLICATIONS

This application claims priority to U.S. Provisional Patent Application Ser. No. 62/025,058 filed Jul. 16, 2014, the entire content of which is hereby incorporated by reference.

TECHNICAL FIELD

This invention relates to medical imaging systems, and more particularly, to real-time image enhancement for X-ray images.

BACKGROUND

In film-screen radiography, an X-ray tube generates a beam of X-rays, which is aimed at a subject. The X-rays that pass through the patient are filtered through a device called an X-ray filter, to reduce scatter and noise, and strike an undeveloped film, which is held tightly to a screen of light-emitting phosphors in a light-tight cassette. The film is then developed chemically and an image appears on the film. In digital radiography, the X-rays strike a plate of sensors, referred to as a detector, that converts the signals generated into digital information, which is transmitted and converted into an image displayed on a computer screen. Accordingly, in a digital radiography system, a projection of the tissue density along the ray path is acquired as a two-dimensional image.

X-ray computed tomography (CT) is a technology that uses computer-processed x-rays to produce tomographic images as virtual slices of specific areas of the scanned object. Digital geometry processing is used to generate a three-dimensional image of the inside of an object from a large series of two-dimensional radiographic images taken around a single axis of rotation. The CT scanning is a measurement of the amount of X-rays absorbed in the specific volume elements constituting the three-dimensional image, and each volume element represents the density of the tissue comprised in the volume element. Medical imaging is the most common application of X-ray CT, and the cross-sectional images generated via CT can be used for diagnostic and therapeutic purposes in various medical disciplines.

Digital tomosynthesis combines digital image capture and processing with simple tube/detector motion as used in computed tomography (CT), however over a smaller rotational angle than that used in CT. One application of digital tomosynthesis is breast tomosynthesis, a three-dimensional imaging technology that involves acquiring images of a stationary compressed breast at multiple angles during a short scan. The individual images are then reconstructed into a series of thin high-resolution slices that can be displayed individually or in a dynamic mode. Reconstructed tomosynthesis slices reduce or eliminate the problems caused by tissue overlap and structure noise in single slice two-dimensional mammography imaging.

SUMMARY OF THE INVENTION

In accordance with an aspect of the present invention, an X-ray imaging system is provided. An X-ray source is configured to provide X-ray radiation and has an associated focal spot. A detector is configured to generate a digital image representing attenuation of the X-ray radiation as it passes through a subject. An image enhancement component is configured to apply a separable deconvolution kernel to the digital image. The kernel is derived from an estimate of the point spread function associated with the focal spot and an estimate of the intrinsic high frequency spatial noise characteristics of the digital image.

In accordance with another aspect of the present invention, a method is provided for image enhancement in real-time. A subject, positioned between a radiation source and a detector, is irradiated with X-ray radiation. Received radiation is measured at the detector to determine an attenuation of the X-ray radiation passing through the subject as a digital image. An image enhancement component is configured to apply a separable deconvolution kernel to the digital image. The kernel is derived from an estimate of the point spread function associated with the focal spot and an estimate of the intrinsic high frequency spatial noise characteristics of the digital image.

In accordance with yet another aspect of the present invention, a method is provided for determining a separable deconvolution kernel for a radiation source associated with an X-ray imaging system. A point spread function of the radiation source is determined. A separable deconvolution function is estimated from the determined point spread function. The separable deconvolution kernel is determined from one of a single variable and a multivariable function derived from the separable deconvolution function.

DETAILED DESCRIPTION

In accordance with an aspect of the present invention, an X-ray imaging system is provided utilizing a separable kernel to apply image correction to an X-ray image. Specifically, a deconvolution kernel is derived from properties of the focal spot of the X-ray tube and the intrinsic high frequency noise characteristics of the digital image, and expressed as a combination of two separable functions. In one example one of the functions is a Gaussian smoothing function, and a second function is a Laplacian sharpening function. Both are applied simultaneously to allow greater spatial resolution, while maintaining acceptable image noise characteristics. Since the functions are separable, the deconvolution kernel can be expressed as a one-dimensional vector, which can be applied in a computationally efficient manner, allowing for pipelined image correction. It will be appreciated that this invention can be used in any digital X-ray imaging system, including computed tomography devices, to enhance the appearance of captured images.

It should be noted that, through this application, the term "substantially" is intended to allow for deviations from the descriptor that do not negatively impact the intended purpose. It should be assumed that the description of any element in this application includes an implicit "substantially" unless specifically disclaimed or is nonsensical in context. For example, the phrase "wherein the lever extends vertically" should be read as "wherein the lever extends substantially vertically" so long as a precise vertical arrangement is not necessary for the lever to perform its function. The terms "comprising" and "including" and "having" and "involving" (and similarly "comprises", "includes," "has," and "involves") and the like are used interchangeably and have the same meaning. Specifically, each of the terms is used as an open term meaning "at least the following," and does not exclude additional features, limitations, aspects, etc. Thus, for example, "a process involving steps a, b, and c" means that the process includes at least steps a, b and c. Wherever the terms "a" or "an" are used, "one or more" is understood, unless such interpretation is nonsensical in context.

Figure 1:
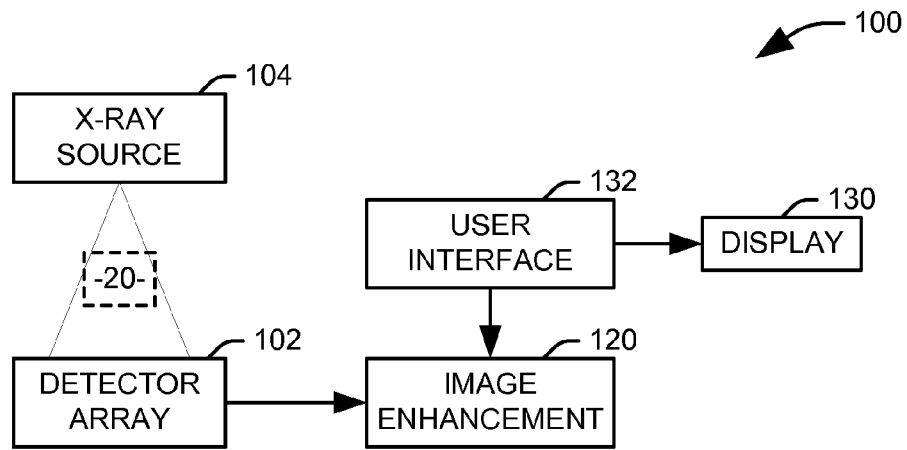
FIG. 1 illustrates an X-ray imaging system in accordance with an aspect of the present invention.

FIG. 1 illustrates an X-ray imaging system apparatus 100 with a subject 20 positioned between a digital detector array 102 and an X-ray source 104. For example, the X-ray imaging system can be a standard digital radiography system, a computed tomography (CT) system, or a digital tomosynthesis system. In the X-ray source, X-rays may be produced by an electron beam at an anode side and accelerated towards and impacting a target at a cathode side. The point where the electron beam impacts the target is called the focal spot. At the focal spot, X-rays are emitted in all directions including towards a small window in the X-ray tube. This window allows the X-ray to exit the tube with little attenuation while maintaining a vacuum seal required for the X-ray tube operation.

The emitted radiation passes through the subject 20 and is captured at a digital detector array 102. The digital detector array 102 captures a two-dimensional digital image representing the attenuation of the radiation as it passes through the subject. This digital image is then provided to a real-time image enhancement system 120. It will be appreciated that the radiation source in an actual X-ray apparatus is not a point source but an elongated rectangle with an angular placement with respect to the image plane. Since there is a finite focal spot size, a certain amount of "focal spot blur" will be present in any image generated at by system 100.

In accordance with an aspect of the present invention, the image enhancement system 120 applies a separable deconvolution kernel to the image to remove image distortion caused by focal spot blur. The deconvolution kernel can be generated, for example, by producing an estimate of the point spread function of the system 100 as a separable and invertible function. In other words, the point spread function is estimated as a function f(x, y) that can be expressed as a product of functions g(x) and h(y). The deconvolution kernel can be determined from an inverse of either or both of the separable functions, or equivalently, a separable function of the inverse of the point spread function.

It will be appreciated that, by using a separable convolution kernel, the image enhancement can be performed with a substantial reduction in calculation time, allowing for near-real time generation of the enhanced images. In one implementation, the deconvolution kernel can be applied as a one-dimensional vector of eighteen values applied to each row of the digital captured image followed by application to each column such that each pixel in the enhanced image, with the possible exception of some pixels near the edge of the image, is a weighted linear combination of 324 pixels from the captured image.

In real-time image processing, deconvolution is often not feasible due to the typical N-squared computational cost, where N is the kernel size. The method proposed herein reduces this cost to 2N computations. Additionally, typical image enhancement accentuates image noise characteristics equivalently to physical edge characteristics captured in the digital image. Noise is often reduced by averaging. This is the same as the application of an N=2 or N=3 kernel. Larger averaging kernels are both computationally cost prohibitive and nonphysically blur the image. The concurrent application of a Gaussian smoothing filter with the Laplacian sharpening filter provides significant digital image enhancement while maintaining computational cost efficiency. Lastly, this invention measures the units of deconvolution filter spatial extent in digital detector pixels. This allows additional computational simplification. The deconvolution filter vector can be precomputed once for all image pixels and applied without interpolation using integer coefficients.

One example of a separable kernel, shown below as Table 1, can be generated via the following equations:

$$\text{Cell}(D_x, D_y) = \frac{S * (D_x^2 + D_y^2 - W^2)}{W^2} e^{\frac{-(D_x^2 + D_y^2)}{N^2}} \qquad \text{Eq. 1}$$

$$\text{Cell}(0, 0) = C * S \qquad \text{Eq. 2}$$

where Cell($D_x$, $D_y$) is the deconvolution coefficient at an offset from an image pixel(x, y) with the offset measured in pixels in x and y directions, W is the full width at half maximum of the beam cross sectional width in units of pixels, N is an estimate of the noise spread measured in units of pixels, S is a scale factor to simplify presentation of the kernel values, and C is a user selectable scale factor to optimize the image contrast relative to image enhancement. The full width at half maximum may be adjusted by a user to optimize deconvolution of X-ray focal spot blurring, and the noise spread estimate can be adjusted by the user to optimize noise filtering. All Cell($D_x$, $D_y$) coefficients are normalized to unity upon application to the image being enhanced.

TABLE 1

| Dx/D | -8 | -7 | -6 | -5 | -4 | -3 | -2 | -1 | 0 | 1 | 2 | 3 | 4 | 5 | 6 | 7 | 8 |
|---|---|---|---|---|---|---|---|---|---|---|---|---|---|---|---|---|---|
| -8 | 0 | 0 | 0 | 0 | 0 | -0.1 | -0.2 | -0.2 | -0.2 | -0.2 | -0.2 | -0.1 | 0 | 0 | 0 | 0 | 0 |
| -7 | 0 | 0 | 0 | -0.1 | -0.2 | -0.4 | -0.7 | -1 | -1.1 | -1 | -0.7 | -0.4 | -0.2 | -0.1 | 0 | 0 | 0 |
| -6 | 0 | 0 | -0.1 | -0.3 | -0.8 | -1.7 | -2.7 | -3.6 | -3.9 | -3.6 | -2.7 | -1.7 | -0.8 | -0.3 | -0.1 | 0 | 0 |
| -5 | 0 | -0.1 | -0.3 | -1 | -2.5 | -4.6 | -7 | -8.7 | -9.3 | -8.7 | -7 | -4.6 | -2.5 | -1 | -0.3 | -0.1 | 0 |
| -4 | 0 | -0.2 | -0.8 | -2.5 | -5.5 | -9.3 | -12 | -13 | -14 | -13 | -12 | -9.3 | -5.5 | -2.5 | -0.8 | -0.2 | 0 |
| -3 | -0.1 | -0.4 | -1.7 | -4.6 | -9.3 | -13 | -13 | -7.2 | -4.1 | -7.2 | -12 | -13 | -9.3 | -4.6 | -1.7 | -0.4 | -0.1 |
| -2 | -0.2 | -0.7 | -2.7 | -7 | -12 | -12 | 0 | 20.1 | 30.3 | 20.1 | 0 | -12 | -12 | -7 | -2.7 | -0.7 | -0.2 |
| -1 | -0.2 | -1 | -3.6 | -8.7 | -13 | -7.2 | 20.1 | 58.4 | 77.2 | 58.4 | 20.1 | -7.2 | -13 | -8.7 | -3.6 | -1 | -0.2 |
| 0 | -0.2 | -1.1 | -3.9 | -9.3 | -14 | -4.1 | 30.3 | 77.2 | 100 | 77.2 | 30.3 | -4.1 | -14 | -9.3 | -3.9 | -1.1 | -0.2 |
| 1 | -0.2 | -1 | -3.6 | -8.7 | -13 | -7.2 | 20.1 | 58.4 | 77.2 | 58.4 | 20.1 | -7.2 | -13 | -8.7 | -3.6 | -1 | -0.2 |

TABLE 1-continued

| Dx/D | -8 | -7 | -6 | -5 | -4 | -3 | -2 | -1 | 0 | 1 | 2 | 3 | 4 | 5 | 6 | 7 | 8 |
|---|---|---|---|---|---|---|---|---|---|---|---|---|---|---|---|---|---|
| 2 | -0.2 | -0.7 | -2.7 | -7 | -12 | -12 | 0 | 20.1 | 30.3 | 20.1 | 0 | -12 | -12 | -7 | -2.7 | -0.7 | -0.2 |
| 3 | -0.1 | -0.4 | -1.7 | -4.6 | -9.3 | -13 | -12 | -7.2 | -4.1 | -7.2 | -12 | -13 | -9.3 | -4.6 | -1.7 | -0.4 | -0.1 |
| 4 | 0 | -0.2 | -0.8 | -2.5 | -5.5 | -9.3 | -12 | -13 | -14 | -13 | -12 | -9.3 | -5.5 | -2.5 | -0.8 | -0.2 | 0 |
| 5 | 0 | -0.1 | -0.3 | -1 | -2.5 | -4.6 | -7 | -8.7 | -9.3 | -8.7 | -7 | -4.6 | -2.5 | -1 | -0.3 | -0.1 | 0 |
| 6 | 0 | 0 | -0.1 | -0.3 | -0.8 | -1.7 | -2.7 | -3.6 | -3.9 | -3.6 | -2.7 | -1.7 | -0.8 | -0.3 | -0.1 | 0 | 0 |
| 7 | 0 | 0 | 0 | -0.1 | -0.2 | -0.4 | -0.7 | -1 | -1.1 | -1 | -0.7 | -0.4 | -0.2 | -0.1 | 0 | 0 | 0 |
| 8 | 0 | 0 | 0 | 0 | 0 | -0.1 | -0.2 | -0.2 | -0.2 | -0.2 | -0.2 | -0.1 | 0 | 0 | 0 | 0 | 0 |

The symmetry of this deconvolution kernel can be exploited by separately applying the central vector to the rows and then subsequently to columns of the image pixels to reduce computational costs. Accordingly, the image enhancement component 120 is configured to apply the separable deconvolution kernel by applying a first one-dimensional vector followed by a second one-dimensional vector, with the second one-dimensional vector being the transpose of the first one-dimensional vector.

The filtered image is provided to a user at an associated display 130 via a user interface 132. In accordance with an aspect of the present invention, a user can utilize the user interface 132 to tune the image to a desired degree of enhancement or to apply multiple forms of image enhancement. To this end, multiple separable kernels can be provided to the image enhancement system 120. The weights associated with each kernel can be tuned by the user allowing for the image or CT reconstruction to be adjusted to a specific application in real time. Perceived noise content and edge contrast may be adjusted independently.

In one implementation, edge enhancement can be applied at the image enhancement system 100 to counteract the focal spot blur from the imaging system 100. Edge enhancement is an image processing filter that enhances the edge contrast of an image or video in an attempt to improve its apparent sharpness. The typical small kernel filter works by identifying sharp edge boundaries in the image, such as the edge between a subject and a background of a contrasting color, and increasing the image contrast in the area immediately around the edge. This has the effect of creating subtle bright and dark artifacts on either side of any edges in the image, called overshoot and undershoot, leading the edge to look more defined when viewed from a typical viewing distance. In the illustrated implementation, the edge enhancement kernel can be determined as a discrete Laplacian operator. The image can also be filtered to mitigate high frequency noise from the image. In the illustrated system 100, a Gaussian function is used for filtering. It will be appreciated that this can be performed independently of or in concert with the edge enhancement. Image artifacts are reduced or non-existent due to the concurrent large kernel Gaussian smoothing. This mechanism may be selected to minimize random noise while preserving physically valid image characteristics.

Figure 2:
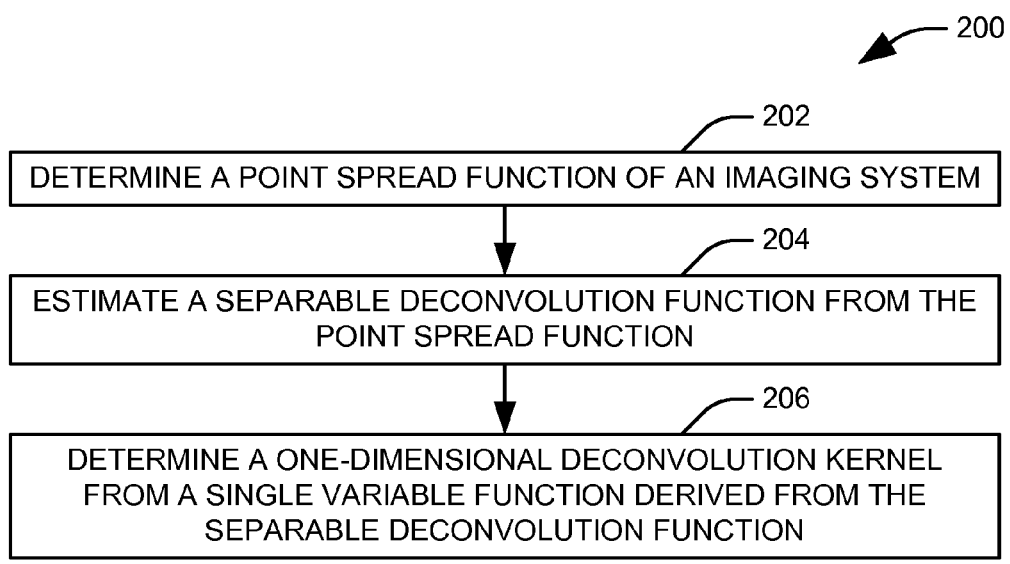
FIG. 2 illustrates a method for determining a deconvolution kernel for an imaging system in accordance with an aspect of the present invention.
Figure 3:
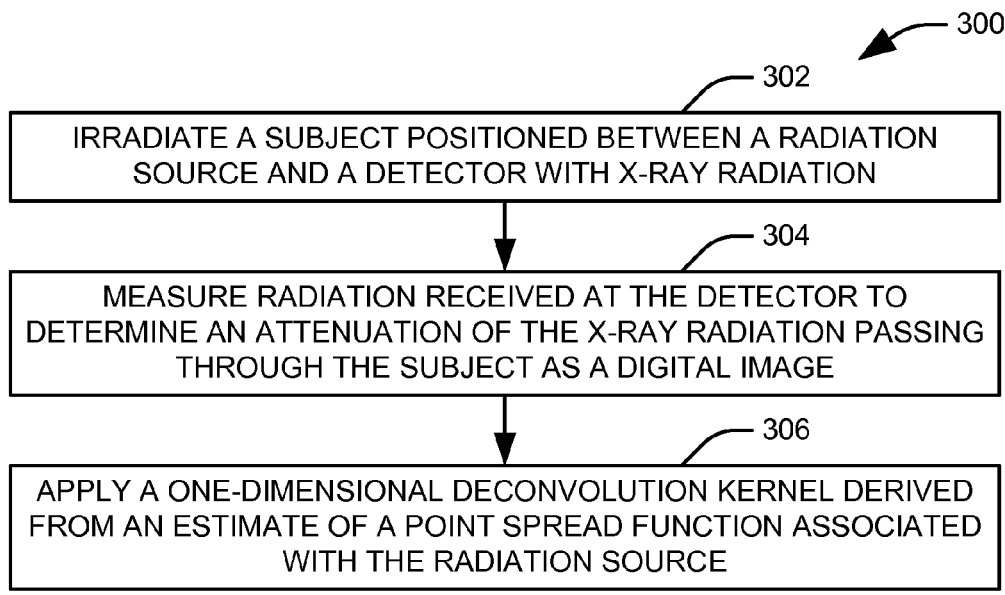
FIG. 3 illustrates a method for providing an enhanced image in real-time in accordance with an aspect of the present invention.

In view of the foregoing structural and functional features described above in FIG. 1, example methodologies will be better appreciated with reference to FIGS. 2 and 3. While, for purposes of simplicity of explanation, the methodologies of FIGS. 2 and 3 are shown and described as executing serially, it is to be understood and appreciated that the present invention is not limited by the illustrated order, as some actions could in other examples occur in different orders and/or concurrently from that shown and described herein.

FIG. 2 illustrates a method 200 for determining a deconvolution kernel for an imaging system in accordance with an aspect of the present invention. At 202, a point spread function of the imaging system is determined. For example, the X-rays can be provided through a pinhole collimator and the resulting image at a detector can be used to determine the point spread function. At 204, at least one separable deconvolution function is estimated from the point spread function. The point spread function can be modeled as noise that has been convolved with the ideal image to produce the image obtained at the detector. Accordingly, a deconvolution function is determined to deconvolve the noise from the ideal image, and can be determined from an inverse of the point spread function.

In one implementation, there are two functions utilized to provide deconvolution kernels for image enhancement. A discrete Laplacian operator derived from the point spread function can be used for edge enhancement. A Gaussian function can be used for noise filtering the image. In accordance with an aspect of the present invention, both functions are selected to be both uniformly smooth, preventing discontinuities, and separable. The fact that both functions are multi-dimensional and uniformly smooth prevents many of the artifacts inherent in small kernel approximations.

At 206, a separable deconvolution kernel, representing multiple variable functions approximating the system focal spot blur and the high frequency noise content of an image is determined. It will be appreciated that the separabililty of the function allows the correction to take place in real time. Specifically, using a separable kernel allows each computed pixel in the deconvolution to be computed as a row and them separately as a column, allowing the computation to be reduced to 2N multiplications and additions per image pixel, where each of a length and width of the kernel is an integer value N. In one example, the separable deconvolution kernel comprises a symmetric N×N matrix, wherein N is an odd integer, and a horizontal vector, representing a first one-dimensional kernel for the X-ray imaging system can be generated as an $$\left(\frac{N+1}{2}\right)^{th}$$

row of the matrix. A corresponding vertical vector, representing a second one-dimensional kernel for the X-ray imaging system, as an $$\left(\frac{N+1}{2}\right)^{th}$$

column of the matrix. An algorithm using this separable kernel approach can be utilized in a pipeline processor in a digital x-ray system to produce real-time images.

FIG. 3 illustrates a method 300 for providing an enhanced image in real-time in accordance with an aspect of the present invention. At 302, a subject is positioned between a radiation source and a detector and irradiated with X-ray radiation. At 304, received radiation at the detector is measured to determine an attenuation of the X-ray radiation passing through the subject and recorded as a digital image. At 306, a separable deconvolution kernel is applied to the digital image. In accordance with an aspect of the present invention, the deconvolution kernel is derived from an estimate of a point spread function associated with a focal spot of the radiation source as a separable function, to the digital image. In one implementation, one of a horizontal and a vertical vector can be applied as a kernel to the digital image followed by the other of the horizontal and the vertical vector, such that the deconvolution kernel is applied as two one-dimensional vectors. In one example, the horizontal vector is the transpose of the vertical vector.

In one implementation, the separable deconvolution kernel can represent a series of weights tunable by a user via a user interface. Accordingly, a degree of edge enhancement provided by the kernel can be controlled by the user in real time to provide an image optimal for a desired application. To this end, it will be appreciated that a number of image enhancement functions, each represented by a separable kernel, can be available to the user, allowing for the image properties to be substantially optimized during a session of imaging. The enhanced image can then be provided to the user at an associated output device, such as a display.

Figure 4:
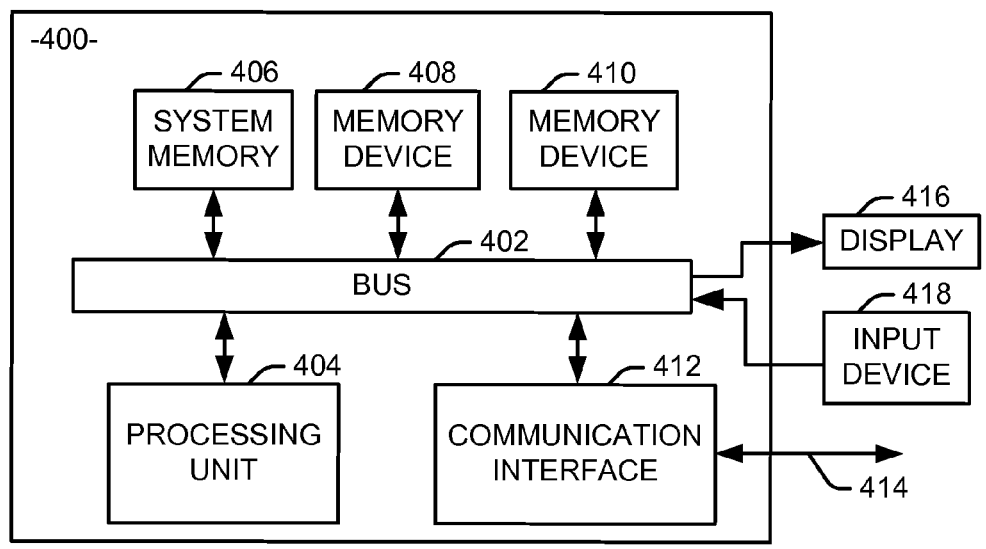
FIG. 4 is a schematic block diagram illustrating an exemplary system of hardware components capable of implementing examples of the systems and methods disclosed in FIGS. 1-3.

FIG. 4 is a schematic block diagram illustrating an exemplary system 400 of hardware components capable of implementing examples of the systems and methods disclosed in FIGS. 1-3, such as the X-ray imaging system illustrated in FIG. 1. The system 400 can include various systems and subsystems. The system 400 can be a personal computer, a laptop computer, a workstation, a computer system, an appliance, an application-specific integrated circuit (ASIC), a server, a server blade center, a server farm, etc.

The system 400 can includes a system bus 402, a processing unit 404, a system memory 406, memory devices 408 and 410, a communication interface 412 (e.g., a network interface), a communication link 414, a display 416 (e.g., a video screen), and an input device 418 (e.g., a keyboard and/or a mouse). The system bus 402 can be in communication with the processing unit 404 and the system memory 406. The additional memory devices 408 and 410, such as a hard disk drive, server, stand alone database, or other non-volatile memory, can also be in communication with the system bus 402. The system bus 402 interconnects the processing unit 404, the memory devices 406-410, the communication interface 412, the display 416, and the input device 418. In some examples, the system bus 402 also interconnects an additional port (not shown), such as a universal serial bus (USB) port.

The processing unit 404 can be a computing device and can include an application-specific integrated circuit (ASIC). The processing unit 404 executes a set of instructions to implement the operations of examples disclosed herein. The processing unit can include a processing core.

The additional memory devices 406, 408 and 410 can store data, programs, instructions, database queries in text or compiled form, and any other information that can be needed to operate a computer. The memories 406, 408 and 410 can be implemented as computer-readable media (integrated or removable) such as a memory card, disk drive, compact disk (CD), or server accessible over a network. In certain examples, the memories 406, 408 and 410 can comprise text, images, video, and/or audio, portions of which can be available in formats comprehensible to human beings.

Additionally or alternatively, the system 400 can access an external data source or query source through the communication interface 412, which can communicate with the system bus 402 and the communication link 414.

In operation, the system 400 can be used to implement one or more parts of an X-ray imaging system in accordance with the present invention, such as the real-time image enhancement system 120 and the user interface 132 of FIG. 1. Computer executable logic for implementing portions of the X-ray imaging system reside on one or more of the system memory 406, and the memory devices 408, 410 in accordance with certain examples. The processing unit 404 executes one or more computer executable instructions originating from the system memory 406 and the memory devices 408 and 410. The term "computer readable medium" as used herein refers to a medium or media that participates in providing instructions to the processing unit 404 for execution. It will thus be appreciated a computer readable medium is non-transitory and can include multiple discrete media that are operatively connected to the processing unit, for example, via one or more of a local bus or an network connection.

What have been described above are examples of the present invention. It is, of course, not possible to describe every conceivable combination of components or methodologies for purposes of describing the present invention, but one of ordinary skill in the art will recognize that many further combinations and permutations of the present invention are possible. While certain novel features of this invention shown and described below are pointed out in the annexed claims, the invention is not intended to be limited to the details specified, since a person of ordinary skill in the relevant art will understand that various omissions, modifications, substitutions and changes in the forms and details of the invention illustrated and in its operation may be made without departing in any way from the spirit of the present invention. Accordingly, the present invention is intended to embrace all such alterations, modifications, and variations that fall within the scope of the appended claims. No feature of the invention is critical or essential unless it is expressly stated as being "critical" or "essential."

What is claimed is:

1. An X-ray imaging system comprising:
   an X-ray source configured to provide X-ray radiation and having an associated focal spot;
   a detector configured to generate a digital image representing attenuation of the X-ray radiation as it passes through a subject;
   an image enhancement component, implemented as machine executable instructions stored on a non-transitory computer readable medium and executed by an associated processor and configured to apply a selected one of a plurality of separable deconvolution kernels, each derived from an estimate of a point spread function associated with the focal spot as a separable function, to the digital image; and
   a user interface that displays the digital image to a user.

2. The X-ray imaging system of claim 1, wherein the estimate of the point spread function is represented as a Laplacian, and the separable deconvolution kernel provides edge enhancement to the digital image.

3. The X-ray imaging system of claim 1, wherein the estimate of the point spread function is represented as a Gaussian function, and the separable deconvolution kernel provides noise filtering to the digital image.

4. The X-ray imaging system of claim 1, wherein the user interface is configured to allow the user to tune weights associated with each of the plurality of separable deconvolution kernels to allow the image to be adjusted to a specific application in real time.

5. The X-ray imaging system of claim 1, wherein the image enhancement component is configured to apply the separable deconvolution kernel by applying a first one-dimensional vector followed by a second one-dimensional vector.

6. The X-ray imaging system of claim 5, wherein the second one-dimensional vector is the transpose of the first one-dimensional vector.

7. The X-ray imaging system of claim 1, wherein the separable deconvolution kernel can be represented as:

$$\text{Cell}(D_x, D_y) = \frac{S*(D_x^2 + D_y^2 - W^2)}{W^2} e^{\frac{-(D_x^2+D_y^2)}{N^2}} ; \text{with Cell}(0,0) = C*S$$

where $\text{Cell}(D_x, D_y)$ is the deconvolution coefficient at an offset from an image pixel(x, y) with the offset measured in pixels in x and y directions, W is the full width at half maximum of the beam cross sectional width in units of pixels, N is an estimate of the noise spread measured in units of pixels, S is a scale factor to simplify presentation of the kernel values, and C is a user selectable scale factor to optimize the image contrast relative to image enhancement.

8. A method for providing an enhanced image in real-time, the method comprising:
   irradiating a subject, positioned between a radiation source and a detector, with X-ray radiation from an X-ray imaging system;
   measuring received radiation at the detector to determine an attenuation of the X-ray radiation passing through the subject as a digital image;
   applying a horizontal vector to the digital image, representing a first one-dimensional kernel for the X-ray imaging system, as an $$\left(\frac{N+1}{2}\right)^{th}$$

row of a symmetric N×N matrix representing a separable deconvolution kernel derived from a point spread function of the radiation source, wherein N is an odd integer, such that after the horizontal vector is applied, a value of a given pixel of a plurality of pixels is equal to a weighted linear combination of the original values of a row of N pixels centered on the given pixel; and
   applying a vertical vector to the digital image, representing a second one-dimensional kernel for the X-ray imaging system, as an $$\left(\frac{N+1}{2}\right)^{th}$$

column of the matrix, such that after the vertical vector is applied, a value of a given pixel of a plurality of pixels is equal to a weighted linear combination of the previous values of a column of N pixels centered on the given pixel.

9. The method of claim 8, further comprising displaying the digital image to a user at an associated output device.

10. The method of claim 8, wherein the horizontal vector is the transpose of the vertical vector.

11. The method of claim 8, wherein the point spread function is represented as a Laplacian, and applying each of the horizontal vector and the vertical vector provides edge enhancement to the digital image.

12. The method of claim 8, wherein the point spread function is represented as a Gaussian function, and applying each of the horizontal vector and the vertical vector provides noise filtering to the digital image.

13. An X-ray imaging system comprising:
   an X-ray source configured to provide X-ray radiation and having an associated focal spot;
   a detector configured to generate a digital image representing attenuation of the X-ray radiation as it passes through a subject; and
   an image enhancement component, implemented as machine executable instructions stored on a non-transitory computer readable medium and executed by an associated processor and configured to apply a separable deconvolution kernel, derived from an estimate of a point spread function associated with the focal spot as a separable function, to the digital image, wherein the separable deconvolution kernel can be represented as:

$$\text{Cell}(D_x, D_y) = \frac{S*(D_x^2 + D_y^2 - W^2)}{W^2} e^{\frac{-(D_x^2+D_y^2)}{N^2}} ;$$

where $\text{Cell}(D_x, D_y)$ is the deconvolution coefficient at an offset from an image pixel(x, y) with the offset measured in pixels in x and y directions, W is the full width at half maximum of the beam cross sectional width in units of pixels, N is an estimate of the noise spread measured in units of pixels, S is a scale factor to simplify presentation of the kernel values, and C is a user selectable scale factor to optimize the image contrast relative to image enhancement.

14. The X-ray imaging system of claim 13, further comprising a user interface configured to display the digital image to a user.

15. The X-ray imaging system of claim 13, wherein the image enhancement component is configured to apply the separable deconvolution kernel by applying a first one-dimensional vector followed by a second one-dimensional vector.

16. The X-ray imaging system of claim 15, wherein the second one-dimensional vector is the transpose of the first one-dimensional vector.

* * * * *